(12) United States Patent
Wang

(10) Patent No.: US 7,897,640 B2
(45) Date of Patent: Mar. 1, 2011

(54) METHOD OF TREATMENT OF VIRUS INFECTIONS USING SHIKONIN COMPOUNDS

(75) Inventor: Feixin Wang, Beijing (CN)

(73) Assignee: Beijing JBC Chinese Traditional Medicine Science and Technology Develop Co. Ltd, Beijing (CN)

( * ) Notice: Subject to any disclaimer, the term of this patent is extended or adjusted under 35 U.S.C. 154(b) by 324 days.

(21) Appl. No.: 11/904,152

(22) Filed: Sep. 26, 2007

(65) Prior Publication Data

US 2008/0182900 A1  Jul. 31, 2008

Related U.S. Application Data

(63) Continuation-in-part of application No. 11/129,255, filed on May 14, 2005, now abandoned, which is a continuation-in-part of application No. PCT/CN03/00138, filed on Feb. 21, 2003.

(51) Int. Cl.
   *A61K 31/215*  (2006.01)
   *A61K 31/12*  (2006.01)
   *A61P 35/00*  (2006.01)

(52) U.S. Cl. ..................................... 514/546; 514/681
(58) Field of Classification Search ....................... None
   See application file for complete search history.

(56) References Cited

FOREIGN PATENT DOCUMENTS

WO  WO 02/076939  * 10/2002

OTHER PUBLICATIONS

Chen et al. Cellular Pharmacology Studies of Shikonin Derivatives. Phytother. Res. 16, 199-209 (May 2002).*

* cited by examiner

*Primary Examiner*—Jeffrey S Lundgren
*Assistant Examiner*—Sara E Clark
(74) *Attorney, Agent, or Firm*—Yi Li

(57) ABSTRACT

Medicaments containing shikonin compounds and salts thereof including shikonin and alkannin are used for treatment of virus infections, mycoplasma infections and malignant tumor.

3 Claims, No Drawings

METHOD OF TREATMENT OF VIRUS INFECTIONS USING SHIKONIN COMPOUNDS

CROSS REFERENCE TO RELATED APPLICATION

This application is a continuation-in-part of patent application Ser. No. 11/129,255, filed May 14, 2005, now abandoned, which is a continuation-in-part application of PCT patent application No. PCT/CN2003/000138, filed Feb. 21, 2003. All parent applications are hereby incorporated by reference in their entirety.

TECHNICAL FIELD

The present invention is directed to shikonin compounds (including shikonin and alkannin), specially shikonin compounds or its salt for preventing and treating microorganism infection in human body, inflammation, tumor, hemorrhage, hematopathy, SARS disease and autoimmune disease. More specifically, the present invention is directed to methods of treating virus infections including hepatitis virus, influenza virus, herpes virus, HIV virus, and SARS virus.

TECHNICAL BACKGROUND

Shikonin compounds have been reported in the literature (Lin Zhibin, et al, P101-105, Issue 2, Volume 12, 1980, JOURNAL OF BEIJING MEDICAL UNIVERSITY), therein, the shikonin compounds have the following general formula structure:

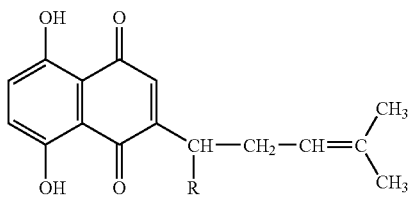

Shikonin compounds are insoluble in water but freely soluble in oil, alcohol or ethers, extracted from Boraginaceae plants: lithospermum erythrorhizo Sieb. et zucc.; Arnebia euchroma (Royle) Johnst. It's known that the Zicao mixture extract has some functions such as anti-inflammation, but it's just mixed in the form of mixture extract when medicament delivers. While it has not been reported that the Zicao quinone compound extracted from plant shikonin and artificial or biosynthetic shikonin quinone compounds are used to manufacture medicaments in single compound or combination of several compounds, particularly for preventing and treating virus infections, such as hepatitis virus, influenza virus, herpes virus, HIV virus, and SARS virus.

DETAILED DESCRIPTION OF THE INVENTION

The present invention is directed to providing a single compound or several compounds separated from Zicao extract to manufacture a medicament for prevention and treatment of microorganism infection in human body, particularly for preventing and treating virus infections, such as hepatitis virus, influenza virus, herpes virus, HIV virus, and SARS virus.

The present invention provides methods for preventing and treating microorganism infections in human body, particularly for preventing and treating virus infections, such as hepatitis virus, influenza virus, herpes virus, HIV virus, and SARS virus, using shikonin compounds or its salt represented in the following Formula (1) as the active component.

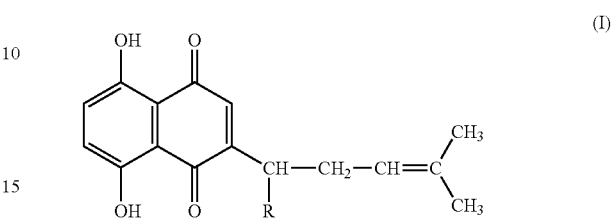

wherein, R is a group selected from a group composed of H(deoxyshikonin), OH(Shikonin), $(CH_3)_2C=CHC(O)O$-($\beta,\beta$-dimethylacry), $CH_3C(O)O$-(acetylshikonin), $(CH_3)_2C=C(CH_3)CH_2C(O)O$-(teracrylshikonin), $(CH_3)_2COHCH_2C(O)$-($\beta$-hydroxyl isovalerylshikonin), $(CH_3)_2C[OC(O)CH_3]CH_2C(O)O$-($\beta$-acetoxyisovalerylshikonin). Preferably, the medicament contains 1 to 3 compounds selected from shikonin, $\beta,\beta$-dimethylacrylshikonin and acetylshikonin; more preferably, the medicament contains $\beta,\beta$-dimethylacrylshikonin and/or acetylshikonin; the most preferably, the medicament contains $\beta,\beta$-dimethylacrylshikonin. The salts of Shikonin compounds in this invention include the salts of alkali metals, alkaline earth metal and ammonium, etc.

The medicament according to this invention contains one or more compound(s) of the shikonin compounds, of which the purity of single compound is 80% or more, and the preferred purity is 90% or more. When the medicine contains a combination of several compounds, the effective components thereof is 70% or more.

If necessary, the invented medicament can further contain other active components. There is no specific restriction to the other active components, which the technologist can select properly in accordance to the existing technology.

The concentration of shikonin compounds in the invented medicament ranges from 0.0001% to 75% (weight percent), which can be selected properly according to different preparation as well as symptoms of disease. When being used in human body, the daily dosage of the mentioned Shikonin compounds can be controlled between 10 μg-20 g, preferably 100 μg-10 g, more preferably 1 mg-8 g, and the most preferred is about 300 mg, which can be selected properly according to the different status such as age, weight and state of illness of different patients. It can be used for a single time or several times. The invented medicament can be delivered in oral administration, external application, injection, inhalation or skin penetration.

The shikonin compounds in the invention can be used for prevention and treatment of microorganism infection including pathogenic Gram-positive *micrococcus*, such as *staphylococcus, streptococcus pneumonia, staphylococcus epidermidis* and *enterococcus*; pathogenic Gram-negative *micrococcus* such as *Klebsiella pneumonia ozaenae, Serratia marcesens, Stenotrophomonas maltophilia*; anaerobic or little aerobic pathogen such as *Helicobacter pylori*; Eumycetes such as deep and superficial eumycetes; *Leuconostoc* spp, *aspergillus fumigatus, cryptococcus, dermatophyte, krusei leuconostoc* spp, *Cercospora punicae*, etc; and all kinds of mycoplasma infection particularly the mycoplasma infection of the respiratory system; virus such as hepatitis B virus, cold virus, herpes virus and HIV virus, SARS virus, such as coronavirus and its variations.

The shikonin compounds can be used for prevention and treatment of inflammation of human body, including phlebitis, vascular purpura, colpitis and edema, etc.

It can also be used for prevention and treatment of hemorrhage and hematopathy in human body, for instance, burning, scalding, various dermatitis, serticemia hemophilia, primary thrombocythemia, leukaemia, etc.

It can also be used for prevention and treatment of tumor especially malignant tumor, for instance, ascitic type tumor: liver cancer, L1210; solid tumor: W256, S180, gastric cancer 823, squamous cell carcinoma 109, Lewis lung cancer, etc.

The medicament containing shikonin compounds in the present invention can be used for prevention and treatment of autoimmune disease of human body, i.e. promoting human body's functions of nonspecific immunity and idiosyncratic cell-mediated immunity through improving the function of immune response of T lymphocytes.

Therefore, the medicament according to the present invention are available for respiratory system, digestive system, urinary system, reproductive system, blood system, circulating system and skin or mucous membrane in human body.

EXAMPLES

The following text provides a detailed description of the preparation of the medicine containing shikonin compounds and pharmacodynamic experiments of the present invention. It will be understood that the following examples are illustrative of the invention and are in no way to be interpreted as limiting the scope of the invention, as defined in the claims.

Preparation Example 1

Shatter 2 kg of Arnebia euchroma (Royle) Johnst and extract with petroleum ether until solution is colorless. Recover from the solvent and obtain 80 g of a dark red paste. Separate the paste using silica gel H-column liquid chromatography using gradient elution with 1%-20% ethyl acetate-petroleum ether to obtain 7 shikonin compounds stated above, i.e. 2.944 g deoxyshikonin (yield is 3.68%), 0.712 g shikonin (yield is 0.89%), 29.024 g β,β-dimethylacrylShikonin (yield is 36.28%), 13.27 g acetylshikonin (yield is 16.59%), 6.032 g teracrylshikonin (yield is 7.54%), 0.776 g β-hydroxyisovaleryshikonin (yield is 0.97%), 0.792 g β-acetoxyisovalerylshikonin (yield is 0.99%). As analyzed by high pressure liquid chromatography, the purities of all fractions are above 90%.

Preparation Example 2

Shatter 2 kg of Arnebia euchroma (Royle) Johnst and filter using 20-40 meshes screen, and obtain 70 g of a red ointment by $CO_2$ supercritical extraction. Separate the cream by high-pressure liquid preparative chromatography (Germany Knauer K1001 type) with preparative column: silica gel H 10 μm 50×300 mm and carry out gradient elution with 1%-20% ethyl acetate-petroleum ether, and then obtain 7 shikonin compounds stated above, i.e. 3.486 g deoxyshikonin (yield is 4.98%), 0.707 g shikonin (yield is 1.01%), 30.877 g, β,β-dimethylacrylshikonin (yield is 44.11%), 15.869 g acetylshikonin (yield is 22.67%), 6.034 g teracrylshikonin (yield is 8.62%), 0.91 g β-hydroxyisovalerylshikonin (yield is 1.30%) and 0.77 g β-acetoxyisovalerylshikonin (yield is 1.10%). As analyzed by high pressure liquid chromatography, the purities of all fractions are above 90%.

Implementation Example 1

Manufacture troche with single or several combinations of the above described 7 compounds according to the methods known to those skilled in the art. The troche containing 10%-70% Shikonin compounds can be made.

Take 100 g β,β-dimethylacrylshikonin obtained in Preparation Example 1 or Preparation example 2, 100 g nucleated fiber, 30 g magnesium stearate, and 4 g hydroxypropyl methyl cellulose under the aseptic operation conditions, to make 0.5 g tablets using known technology and equipment.

Implementation Example 2

Manufacture 0.5 g tablets with 100 g combination of Shikonin compounds obtained in Preparation example 1 or Preparation example 2 (proportion of Shikonin, β,β-dimethylacrylshikonin and acetylshikonin is 1:1:2) using the method described in Implementation Example 1.

Implementation Example 3

Manufacture ointment of the above described 7 Shikonin compounds according to the methods known to those skilled in the art. The ointment containing 0.0001%-10% Shikonin compounds can be made. Under the aseptic operation conditions, take 0.5 g Shikonin compounds obtained in Preparation example 1 or Preparation example 2 (proportions of deoxyshikonin, Shikonin, β,β-dimethylacrylshikonin acetylshikonin and β-hydroxyisovalerylshikoninis are 0.7:1:1:2:0.5), 80 g vaseline, 10 g liquid paraffin and 10 g anhydrous lanolin and distribute them equably into products in separate bags for external use. This ointment can also be made into patch for skin penetration according to the methods known to those skilled in the art.

Implementation Example 4

Manufacture the injection solution of the above described 7 Shikonin compounds according to the methods known to those skilled in the art. Under the aseptic operation conditions, take 0.5 g β,β-dimethylacrylshikonin obtained in Preparation example 1 or Preparation example 2, 400 ml propylene glycol, 100 ml ethanol, 20 ml tween-80 and 15 ml benzyl alcohol, dissolve the compounds completely and then add water to 1,000 ml. After thoroughly mixing, bottle them as the injection solution.

The following describes the test results on the effect of shikonin compounds in treating fungi infections.

(1) Preparation of the Medicine

Weigh 5.0 mg of shikonin, β,β-dimethylacrylshikonin, acetylshikonin obtained in Preparation example 1 or Preparation example 2, respectively. Dissolve the compounds in 1 ml DMSO. After diluting by 50 times with RPMI-1640 culture medium, pack them separately and further dilute into the following concentration: 100, 50, 25, 12.5, 6.25, 3.13, 1.56, 0.78, 0.39 (μg/ml).

(2) Sensitivity Test of the Medicine

Separately pack the medicament in the above described concentrations into the orifice plate and vaccinate with all bacterial strains at a density of $10^3$-$10^{6.}$ The test result indicates that shikonin, β,β-dimethylacrylshikonin and acetylshikonin have high sensitivity to Gram-positive *staphylococcus aureus* and the MIC is 0.391-12.5 μg/ml; for Gram-negative pathogen, the MIC of *pneumobacillus* is 0.391-6.25 μg/ml and that of some bacterial strains is 12.5-50 µg/ml; most isolates of bacillus prodigiosus and most bacterial strains of *stenotrophomonas bacilli* have a MIC of 0.391-3.125 µg/ml. Therein, they are especially effective to *stenotrophomonas bacilli* and the MIC is 0.391-0.781 µg/ml while that to berberine is 8-32 µg/ml, i.e. it is better than berberine. For bacteroid, especially *bacteroides fragilis*, the MIC is 0.391-6.25 µg/ml; they are highly sensitive to *Helicobacter pylori* and the MIC is 0.391-0.781 µg/ml.

Additionally, the result of β,β-dimethylacrylshikonin in vitro antifungal test indicates that the MIC for candida and cryptococcus is 2.08-33.3 µg/ml and $MIC_{90}$ is 33.3 µg/ml; for fluconazole the MIC is 0.125-64 µg/ml and $MIC_{90}$ is 69 µg/ml; to dermatophyte the MIC is 4.16-8.32 µg/ml with $MIC_{90}$ of 4.16 µg/ml while the MIC of fluconazole to most bacterial strains of dermatophyte is 32-64 µg/ml with $MIC_{90}$ of 64 µg/ml. There are obvious differences in both of them. Furthermore, β,β-dimethylacrylshikonin has good inhibitory effect to *C. krusei* that resists fluconazole and the MIC is 8.32-16.6 µg/ml, and for *Pseudallescheria boydii* that is insensitive to most antifungal medicaments like fluconazole, the MIC is 4.16-8.32 µg/mi. In addition, the MIC of acetylshikonin against cryptococcus neoformans is 3.90625 µg/ml, against red trichophyton is 0.90625-62.5 µg/ml; the MIC of β,β-dimethylacrylshikonin against *aspergillus fumigatus, cryptococcus* and red trichophyton is 3.0625-250 µg/ml. Therefore, Shikonin compounds are a broad spectrum and effective antifungal drug.

In addition, shikonin compounds of the invention have a MIC of over 200 µg/ml on the microbes like *Lactobacilli* and *Bifidobactirium* beneficial for human body. Therefore, the above data indicates that medicaments with Shikonin compounds of the invention are sensitive to pathogenic microorganism but insensitive to microbes that are beneficial to human body.

From the comparative experiment between the mixed extraction from Zicao and 1-3 types of shikonin compounds, it is observed that the medicaments containing Shikonin compounds are obviously better than mixed extraction from Zicao; the results of MIC (µg/ml) are shown in Table 1.

TABLE 1

| Name of bacterial strain | A | B | C |
| --- | --- | --- | --- |
| *Staphylococcus epidermidis* | 12.5 | 0.391 | 0.7812 |
| *Serratia marcescens* | 25 | 0.781 | 3.125 |
| Bacteroid | >200 | 0.391 | 0.391 |
| *Candida albicans* | 500 | 3.9062 | 250 |

Note:
A is mixed extraction from Zicao;
B is β,β-dimethylacrylshikonin; and
C is mixture of Shikonin compounds (the mixture ratio of Shikonin, β,β-dimethylacrylshikonin and Acetylshikonin is 1:1:2).

The experiment on the bacteriostatic effect of shikonin, β,β-dimethylacrylshikonin and acetylshikonin on mycoplasma pneumoniae shows that their MIC for mycoplasma pneumoniae are 3.751 µg/ml, 2 µg/ml and 7.819 µg/ml, respectively, which are equivalent to the inhibitory effect of 0.1925 µg/ml erythrocin.

The following table shows the test results of using Shikonin compound ointment made in Implementation Example 3 as a topical composition for treating some diseases.

TABLE 2

| Cases | Number of subjects | Effective percentage | Cured percentage | Days of treatment | Medicament Delivery route | Note |
| --- | --- | --- | --- | --- | --- | --- |
| Burn & scalding | 300 | 100% | 100% | 6-20 | Direct delivery at affected part | 92 people scalded, 186 second degree superficial burns, 114 deep second degree and third degree burns |
| Hemorrhoids | 117 | 100% | 97.4% | 15 | Direct delivery at affected part | Recurrence in three cases after half a year |
| Herpes zoster | 98 | 100% | 100% | 3-7 | Direct delivery at affected part | Polyinosinic-polytidylin acid is used in 12 cases |
| Cervical erosion | 80 | 100% | 100% | 10-20 | Vagina delivery | |
| Children's nosebleed | 257 | 99.6% | 72.8% | 15 | Nasal cavity delivery | |
| Verruca plana | 100 | 96% | 81% | 10-30 | Direct delivery at affected part | |
| Chronic prostatitis | 40 | 82.5% | 57.5% | 10-20 | Anus delivery | |
| Acne | 50 | 92% | 60% | 15 | Direct delivery at affected part | |
| Bedsore | 30 | 100% | 100% | 7-21 | Direct delivery at affected part | |
| Eczema rhagadiforme | 98 | 94.9% | 66.3% | 10-30 | Direct delivery at affected part | |
| Verruca acuminata | 55 | 100% | 100% | 5-35 | Direct delivery at affected part | |
| Infantal diaper dermatitis | 208 | 100% | 100% | 2-6 | Direct delivery at affected part | |

It is observed from the above table that the topical composition of Shikonin compounds is suitable for treatment of most abscess, wound, scabies and herpes and the effect is prominent for burn and scalding without cicatrices after recovery.

Table 3 shows the animal test results for using shikonin, β,β-dimethylacrylshikonin and acetylshikonin to treat tumor.

TABLE 3

| Type of tumor | β,β-dimethylacrylshikonin | | Acetylshikonin | | Shikonin | |
|---|---|---|---|---|---|---|
| | Tumor inhibitory rate | Life prolonged rate | Tumor inhibitory rate | Life prolonged rate | Tumor inhibitory rate | Life prolonged rate |
| Ascitic tyre liver cancer | | 113.4% | 47.8% | 112.6% | | 130.8% |
| S180 | 9.63% | | 35.7% | | | |
| Lewis lung cancer | 42.8% | | 52.6% | | | |
| L1210 | | | | 128% | | |
| W256 | | | 77% | | | |

It is observed from the above table that β,β-dimethylacrylshikonin has different extent of therapeutic effect for liver cancer, S180 and Lewis lung cancer; acetylshikonin has different extent of therapeutic effect for liver cancer, S180, L1210 and Lewis lung cancer and W256; Shikonin is only effective for liver cancer.

Shikonin compounds are effective in preventing and treating virus infections. The following describes the effect of shikonin compounds in treating hepatitis virus, HIV and SARS as examples. However, it should be understood that the present invention is not limited to the treatment of these viruses.

Shikonin Compounds' Efficacy in Treating Duck Hepatitis B Virus (DHBV)

1. Material 1.1 Medicament

β,β-dimethyl-acryl-alkannin (AKJ) was dissolved in 2% DMSO and normal saline. Lamivudine (3TC) was made by GSK (lot No.: 0212008).

1.2 Virus:

DNA of duck's hepatitis B virus (DHBV-DNA): strong positive serum, derived from Shanghai sheldrake, stored at −70° C.

1.3 Animal:

1-day-old Beijing ducklings, purchased from Beijing Qianjin Duck Breeding Farm.

1.4 Reagent:

α-32 P-dCTP was purchased from Beijing Furui Biological Engineering Co., Ltd. Nick translation kit was purchased from Promega Co., Sephadex ML-50 and Ficoll PVP were purchased from Sweden Pharmacia Co.; SDS was made by West Germany Merck; milt DNA and bovine serum albumin (BSA) were made by the Institute of Biophysics of the Chinese Academy of Sciences; pyroxylin membrane (0.45 μm) was made by Amersham.

2. Method:

2.1. Infection of DHBV:

1-day-old Beijing ducklings were injected intravenously into the leg vein with DHBV-DNA positive serum from Shanghai Sheldrake (0.2 ml per animal). 7 days after infection, the blood was taken to separate serum, which was stored at −70° C. for further analysis.

2.2 Pharmacotherapy Test:

After DHBV infection, the infected ducklings were randomly divided into groups for pharmacotherapy test, 6 ducks per group. In this test, the treatment groups were divided into 3 dosage groups: 100 mg/kg, 50 mg/kg and 25 mg/kg. The medicaments were administered orally, twice daily for 10 days. A virus control group (DHBV) was established in which normal saline was substituted for the medicament. In addition, another positive control group was also established in which lamivudine (3TC) was orally administered with a dosage of 50 mg/kg, twice per day for 10 days. On the seventh day after infection (i.e., the day before administration of the medicament) (T0), the fifth day during administration (T5), the tenth day during administration (T10) and the third day after cessation of administration (P3), the duck blood was taken from the leg vein, and the serum was separated and stored at −70° C. for further analysis.

2.3 Test Method:

After obtaining the aforesaid duck serum, the serum samples in each lot were dotted on membrane simultaneously to determine the dynamic condition of DHBV-DNA in the duck serum. According to the method described in the instruction book of nick translation kit, DHBV-DNA probe was labeled with 32P, and the Dot-Blot hybridization in serum was carried out. The blots on the film were autoradiographed and OD values were measured using luminometer (the optical filter was 490 nm). In order to determine the density of DHBV-DNA in the serum, the OD values of hybridized blots were used as the level-value of specimen DHBV-DNA.

2.4 Calculation of Efficacy:

1. The average OD values of the serum DNA for each group at different times (X±SD) were calculated, and the serum DHBV-DNA levels of T5, T10 and P3 were compared with the OD value of T0. The values of t1 and p1 were calculated using pairing t test. The significance of difference was analyzed to judge the inhibition effect of the medicament against the virus infection.

2. The inhibition percentages of serum DHBV-DNA of each group on T5, T10 and P3 were calculated, and the dynamic conditions of the serum DHBV-DNA inhibition rate between each group were compared.

3. The inhibition percentages of DHBV-DNA of the test groups at different times were compared with that of the virus control group at the same time. Statistical analysis was performed using grouping t test to calculate the values of t2 and p2. The significance of difference was analyzed to determine the efficacy.

3. Results 3.1. The Dynamic Condition of Serum DHBV-DNA from the DHBV Infected 1-Day-old Beijing Ducklings The DHBV-DNA Dot-Blot hybridization results of DHBV-DNA infected ducklings after oral administration of normal saline are shown in Table 4 and Table 5. In the test, there were totally 90 infected ducklings and their serum DHBV-DNA was all positive. In the virus control group, 7 days after infection, the serum DHBV-DNA of totally 18 ducklings was all positive, and their serum DHBV-DNA levels after being infected were basically stable during 21-day test period.

TABLE 4

The comparison of serum DHBV-DNA OD values between the test groups and the virus control group

| Lot No. | Group | Dosage (mg/kg) | Number of ducklings (pcs) | Serum DHBV-DNA OD490 value (X ± SD) | | | |
|---|---|---|---|---|---|---|---|
| | | | | T0 bid × 10 | T5 | T10 | P3 |
| I | Normal Saline | | 6 | 1.848 ± 0.16 | 1.823 ± 0.16 | 1.878 ± 0.10 | 1.778 ± 0.17 |
| | AKJ | 25 | 6 | 0.851 ± 0.15 | 0.767 ± 0.18 | 0.762 ± 0.15 | 0.792 ± 0.13 |
| | | 50 | 6 | 1.082 ± 0.23 | 0.961 ± 0.23 | 0.680 ± 0.09* | 0.696 ± 0.05* |
| | | 100 | 6 | 1.207 ± 0.23 | 0.987 ± 0.26* | 0.757 ± 0.19** | 0.667 ± 0.22** |
| II | Normal Saline | | 6 | 0.685 ± 0.03 | 0.759 ± 0.07 | 0.708 ± 0.05 | 0.673 ± 0.04 |
| | AKJ | 25 | 6 | 1.005 ± 0.22 | 1.061 ± 0.08 | 0.928 ± 0.09 | 1.092 ± 0.13 |
| | | 50 | 6 | 1.375 ± 0.28 | 1.075 ± 0.14* | 0.947 ± 0.13* | 1.140 ± 0.25 |
| | | 100 | 6 | 1.080 ± 0.21 | 0.872 ± 0.13* | 0.670 ± 0.14** | 0.875 ± 0.17* |
| III | Normal Saline | | 6 | 1.396 ± 0.19 | 1.097 ± 0.14 | 1.610 ± 0.29 | 1.571 ± 0.21 |
| | AKJ | 25 | 6 | 1.263 ± 0.35 | 1.079 ± 0.23 | 1.076 ± 0.16 | 1.035 ± 0.21 |
| | | 50 | 6 | 1.649 ± 0.13 | 1.459 ± 0.28 | 1.411 ± 0.31 | 1.368 ± 0.11** |
| | | 100 | 6 | 1.474 ± 0.38 | 1.351 ± 0.30 | 1.046 ± 0.42* | 1.146 ± 0.56 |
| | 3TC | 50 | 6 | 0.793 ± 0.14 | 0.557 ± 0.29* | 0.521 ± 0.22** | 0.876 ± 0.35 |

Statistical analysis: t1, p1: comparison of serum DHBV-DNA OD values between different times in the test groups (T5, T10 and P3) and the day before administration (T0) (pairing t test).
*p1 < 0.05,
**p1 < 0.01.

TABLE 5

The comparison of Serum DHBV-DNA level inhibition rates between the test groups and the control group

| Lot No. | Group | Dosage (mg/kg) | Number of ducklings (pcs) | Inhibitory Rate (%) | | |
|---|---|---|---|---|---|---|
| | | | | T5 | T10 | P3 |
| I | virus control group | | 6 | 1.09 | −2.02 | 3.61 |
| | AKJ | 25 | 6 | 8.81 | 8.73 | 5.43 |
| | | 50 | 6 | 9.16 | 33.56** | 32.39** |
| | | 100 | 6 | 17.86* | 37.09** | 44.91** |
| II | virus control group | | 6 | −10.79 | −3.39 | 1.76 |
| | AKJ | 25 | 6 | −8.66 | 5.67 | −12.91 |
| | | 50 | 6 | 20.22** | 27.55* | 14.99 |
| | | 100 | 6 | 18.14** | 36.65** | 18.04* |
| III | virus control group | | 6 | −15.41 | −15.82 | −13.50 |
| | AKJ | 25 | 6 | 11.66* | 11.96* | 16.14* |
| | | 50 | 6 | 11.03* | 13.00 | 16.59** |
| | | 100 | 6 | 2.76 | 28.41** | 18.34 |
| | 3TC | 50 | 6 | 32.35** | 35.73** | −7.29 |

Statistical analysis: t2, p2: comparison of serum DHBV-DNA inhibition percentages between the tested groups (T5, T10 and P3 were compared with T0) and the virus control group (grouping t test).
*p2 < 0.05,
**p2 < 0.01.

3.2 Effect of Shikonin Compounds on the Serum DHBV-DNA of the DHBV Infected Ducklings The test results were as follows:

1) In the first lot of tests, AKJ was administered in 3 dosages (see Table 4 and Table 5), which were 100 mg/kg, 50 mg/kg and 25 mg/kg, respectively. At T0, T5, T10 and P3, the duck blood was taken to separate serums for detecting the OD value of DHBV-DNA and for self-comparison. The results indicated that according to the pairing t test, for the 100 mg/kg dosage group, the serum DHBV-DNA of the test groups showed significant and extremely significant decrease ($p<0.05, 0.01$) at T5, T10 and P3. According to the grouping t test, the serum DHBV-DNA of the test groups showed significant and extremely significant decrease at T5, T10 and P3 compared with that of the control group respectively ($p<0.05, 0.01$). For the 50 mg/kg group, according to the pairing t test, significant inhibition effect was shown at T10 and P3 ($p<0.05$). According to the grouping t test, the serum DHBV-DNA of the tested groups showed extremely significant decrease at T10 and P3 compared with that of the control group, respectively ($p<0.01$). No statistical significance was shown for the 25 mg/kg group.

2) In the second lot of tests, AKJ was administered in 3 dosages (see Table 4 and Table 5), which were 100 mg/kg, 50mg/kg and 25 mg/kg, respectively. According to the pairing t test, for the 100 mg/kg group, the serum DHBV-DNA of the test groups showed significant and extremely significant decrease ($p<0.05, 0.01, 0.05$) at T5, T10 and P3. According to the grouping t test, the serum DHBV-DNA of the test groups showed significant and extremely significant decrease at T5, T10 and P3 compared with that of the control group, respectively ($p<0.01, 0.05$). For the 50 mg/kg group, according to the pairing t test, significant inhibition effect was shown on T5 and T10 ($p<0.05$). According to the grouping t test, the serum DHBV-DNA of the test groups showed significant decrease on T10 compared with that of the control group respectively ($p<0.05$). No statistical significance was shown for the 25 mg/kg group.

3) In the third lot of tests, the aforesaid two lots of tests were repeated: AKJ was administered in three dosage (see Table 4 and Table 5), which were 100 mg/kg, 50 mg/kg and 25 mg/kg, respectively. According to the pairing t test, the serum DHBV-DNA of 100 mg/kg test group showed significant decrease at T10 ($p<0.05$). According to the grouping t test, the serum DHBV-DNA of the test groups showed extremely significant decrease at T10 compared with that of the control group respectively ($p<0.01$). For 50 mg/kg group, according to the pairing t test, significant decrease effect was shown on P3 ($p<0.01$). According to the grouping t test, the serum DHBV-DNA of the test groups showed significant and extremely significant decrease at T5 and P3 compared with that of the control group, respectively ($p<0.05, 0.01$). According to pairing t test, no significant difference was shown for the 25 mg/kg group.

In addition, the tests administering shikonin mixtures were carried out, the tenth day after the administration of 100 mg/kg shikonin mixtures (T10), the serum DHBV-DNA of the test group showed significant decrease ($p<0.05$). According to the grouping t test, the serum DHBV-DNA of the test groups showed significant decrease at T10 and P3 compared with that of the control group, respectively ($p<0.05$). The fifth day and the tenth day after the administration of 50 mg/kg positive medicament Lamivudine (3TC) (T5 and T10), the serum DHBV-DNA of the test groups showed significant and extremely significant decrease ($p<0.05, 0.01$).

Shikonin Compounds' HIV-1 Inhibition Effect in Cell Culture

1. Material

1.1 Medicament

Shikonin compound samples were provided by Beijing JBC Traditional Chinese Medicine Technology Development Co., Ltd. β,β-dimethyl-acryl-alkannin (AKJ-1) and acetylshikonin (AKJ-2) (lot No.: 030602) were pure compounds, solid powder with modena crystal color. The samples were insoluble in water but soluble in DMSO. In the test, they were dissolved in DMSO at 100 µg/ml, and diluted to the tested concentrations with cell culture fluid.

Positive control group: anti-HIV-1 reverse transcriptase inhibitor, Zidovudine (AZT) was purchased from Shanghai Desano Chemical Pharmaceutical Co., Ltd. (lot No.: 040201b).

1.2 Cell

The passage human T lymphocytes MT-4 was stored in the lab. Human peripheral blood mononuclear cell (PBMC) was separated from the healthy fresh venous blood. The human T lymphocytes H9 passage cell strain chronically infected with HIV-1IIIB virus was donated by Zhang Xingquan, the professor of the Contagion Department of Colorado University, US. MT-4 cell was incubated with RPMI medium 1640 culture medium containing 10% fetal bovine serum, 100 IU/ml penicillin, 100 µg/ml streptomycin and kanamycin, as well as containing L-glutamine in the incubator (37° C., 5% $CO_2$); the cell strain was subcultured once every three days.

Ingredients of PBMC culture fluid: 20 ml fetal bovine serum, 300 µg phytohemagglutinin, 1000 U interleukin-2 and 2 ml bacteriophage (10,000 U/ml penicillin, streptomycin and kanamycin respectively) were added to 100 ml RPMI medium 1640 culture fluid.

The Passage human T lymphocytes H9 cell strain chronically infected with HIV-1IIIB virus cell was donated by Professor Zhang Xingquan and stored in the lab. The H9 cell strain was incubated with RPMI medium 1640 culture medium containing 10% fetal bovine serum, 100 IU/ml penicillin, 100 µg/ml streptomycin and kanamycin as well as containing L-glutamine in the incubator (37° C., 5% $CO_2$); the cell strain was subcultured once every three-four days.

1.3 Virus

The passage HIV-1IIIB viral strain in the lab was subcultured in the aforesaid chronic infected human T lymphocyte H9 passage cell strain, stored in liquid nitrogen.

Clinically-separated AZT-sensitive strain HIV-1 018a and AZT-resistant strain HIV-1 018c were donated by Zhang Xingquan and were subcultured in PBMC cells in the lab.

1.4 Main Test Reagents

RPMI Medium 1640 (powder) culture medium was produced by GIBCO Co., US. Fetal bovine serum was produced by GIBCO Co., US. Penicillin, streptomycin and kanamycin were produced by Shandong Qilu Pharmaceutical Factory. Thiazolyl blue (MTT), citric acid, was produced by Sigma Co., US. Triton X-100 was produced by KEBO AB STOCK-HOLM Co. N,N-dimethyl formamide was produced by Beijing Chemical Plant. HIV-1 P24 antigen test kit was produced by ZeptoMetrix Co., US.

1.5 Instruments

Emax™ luminometer was produced by Molecuar DevECes Co., US. The tests were carried out in 3-level biosafety lab.

2. Method

2.1 Measurement of Cytotoxicity and HIV-1-P24 Antigen Inhibition Effect of AKJ-1 and AKJ-2 in the Cell Culture

2.1.1 Culture of Passage Human T Lymphocyte MT-4 Cells (1) Experimental Method of Concurrently Medicating for Measuring the Cytotoxicity and Efficacy MT-4 cell suspension was counted, then 100 µl of suspension ($2 \times 10^5$ cells/ml) was seeded into 96-well cell culture plate, 50 µl liquor of 2× diluted medicament or 4-5× diluted positive medicament AZT (8 concentrations) was added, respectively, and 50 µl virus suspension with proper titer was add concurrently. Each dilution was repeated in 3 wells and cell control group and virus control group were established. They were incubated at 37° C., 5% $CO_2$ saturated humidity incubator and the cytopathy was observed everyday. On the fourth day after administration (96 hours), the supernatants were sucked out and stored at −20° C. for measuring HIV-1-P24 antigen titer. Accordingly, the inhibition effect of medicament could be calculated, and the cells were dyed with MTT to measure the cytotoxicity.

(2) Measure of Cytotoxicity Using MTT Dye

10 µl MTT dye (5 mg/ml) was added to each well, and then incubated at 37° C., 5% $CO_2$ saturated humidity incubator for 4 hours. 100 µl 50% DMF-17% Triton X-100 destainer was added to each well and the mixtures were kept at 37° C. overnight. Then $OD_{570nm}$ values were measured at 570 nm with a luminometer to calculate the median cytotoxicity concentration of medicament ($CC_{50}$).

(3) Measure of the Median Effective Concentration ($EC_{50}$) of Medicament for Inhibiting HIV-1 P24 Antigen in the Cell Culture The medicated cell supernatants infected with MT-4 were diluted after being thawed. HIV-1 P24 titer was measured according to the operation procedure described in HIV-1 P24 antigen kit. Comparing the test groups and virus control group, the median effective concentration of medicament ($EC_{50}$) can be determined.

2.1.2 Culture of HIV-infected PBMC Cell (1) Experimental Method for Measuring the Cytotoxicity and Efficacy by Medicating 2 Hours After HIV Virus Infection The fresh normal human venous blood was taken and PBMC was separated using FiColl separation solution. The $1.5 \times 10^5$ cells/ml suspension prepared with the culture fluid containing PHA was seeded into the culture bottle and incubated in the incubator (37° C., 5% $CO_2$) for 72 hours. The cells were collected with cell scrapers then were infected with the $10^{-2}$ viral liquid of AZT-sensitive (018a) or AZT-resistant (018c) viral strain. After absorption for 2 hours, the non-absorbed viruses were washed with serum-free 1640 culture medium. The infected cells were prepared into $1 \times 10^6$ cells/ml with the culture fluid, and then were seeded into the 96-well culture board in 100 µl/well. At the same time, 100 µl liquor of 2× diluted AKJ-2 or 5× diluted positive control medicament AZT with different concentrations was added. The cell control group and virus control group were established. Four days (96 hours) after incubating under 37° C., 5% CO2, the supernatants were sucked out and stored at −20° C. to measure HIV-1-P24 antigen titer and calculate the inhibition effect of the medicament. The cells were dyed with MTT to measure the cytotoxicity.

(2) The MTT Method for Measuring Cytotoxicity

The method is the same as the culture of MT4 cell described above.

(3) ELISA Method for Measuring HIV-1 P24 Antigen

The medicated cell supernatants infected with PMBC which were stored in frozen state were diluted after being thawed, and the ratio of dilution was adjusted according to the pre-test results. HIV-1 P24 antigen titer was measured according to the operation procedures stated in HIV-1 P24 antigen kit. Comparing the test groups and the virus control group, the median effective concentration ($EC_{50}$) of the medicament or the positive control medicament AZT can be determined.

2.1.3 The Human T-lymphocytes H9 Passage Cells Chronically Infected with HIV-1IIIB Virus (1) Experimental Method for Measuring the Cytotoxicity and Efficacy by Medicating in H9 Cells Chronically Infected with HIV-1

100 µl ($2 \times 10^5$ cells/ml) of H9 cells suspension was seeded into 96-well cell culture plate. Then, 100 µl liquor of 2× diluted medicament or 4-5× diluted positive AZT (8 concentrations) was added. Each dilution was repeated in three wells. The cell control group was established. The cells were incubated in the incubator (37° C., 5% $CO_2$, saturated humidity) and the cytopathy was observed everyday. Four days (96 hours) after administration, the supernatants were sucked out and stored at −20° C. to measure HIV-1-P24 antigen titer. The inhibition effect of the medicament was determined. The cells were dyed with MTT to measure the cytotoxicity.

(2) The MTT Method for Measuring Cytotoxicity

The method is the same as the culture of MT-4 cell described above.

(3) ELISA Method for Measuring HIV-1 P24 Antigen

The method is the same as that used for PBMC cells described above.

2.2 Calculation Method of Median Cytotoxicity Concentration ($CC_{50}$) and Median Effective Concentration ($EC_{50}$) and Selection Index (SI)

2.2.1 Calculation Method of Inhibition Percentage on Cells or HIV-1 P24 Antigen in Cell Culture Inhibition percentage =

$$\frac{OD \text{ of test group} - OD \text{ of virus control group}}{OD \text{ of normal control group} - OD \text{ of virus control group}}$$

2.2.2 Reed & Muench Method for Calculating $CC_{50}$ and $EC_{50}$ of Medicament in Cell Culture The formula is as follows:

$$CC_{50} \text{ or } CE_{50} = \text{Anti log}\left(\log < 50\% \text{ medicament concentration} + \frac{50 - < 50\% \text{ accumulative inhibition \%}}{> 50\% \text{ accumualtive inhibition (\%)} - < 50\% \text{ accumative inhibition (\%)}} * \log \text{ dilution times}\right)$$

2.2.3. Calculation Method of Selection Index (SI) of HIV-1 P24 Antigen in Cell Culture $SI = CC_{50}/EC_{50}$

3. Results

The cytotoxicity and inhibition effect of AKJ-1 on HIV-1 and AKJ-2 on HIV-1 virus IIIB test strain in the passage human T-lymphocytes MT-4 culture, the clinically-separated AZT sensitive HIV-1 018a and AZT-resistant HIV-1 018c viral strain in human PBMC culture, as well as in H9 cell culture chronically infected with HIV-1 IIIB, were summarized in Table 6.

TABLE 6

The cytotoxicity and inhibition effect on HIV-1 of meidicaments in Cell Culture

| Cell culture | Viral strain | medicament | Median cytotoxicity concentration (µg/ml) | Median effective concentration (µg/ml) | Selection index |
|---|---|---|---|---|---|
| Human T-lymphocytes MT-4 | HIV-1 IIIB | AKJ-1 | 0.31 ± 0.04 | 0.07 ± 0.01 | 4.49 ± 0.94 |
| | | AKJ-2 | 0.49 ± 0.06 | 0.20 ± 0.03 | 2.45 ± 0.51 |
| | | AZT | 14.01 ± 1.17 | 0.09 ± 0.003 | 1808.33 ± 723.07 |
| PBMC | AZT-Sensitive HIV-1 018a | AKJ-1 | 5.66 ± 0.28 | 1.11 ± 0.11 | 5.12 ± 0.33 |
| | | AKJ-2 | 7.69 ± 0.19 | 1.18 ± 0.03 | 6.50 ± 0.08 |
| | | AZT | 77.18 ± 20.94 | <0.0064 ± 0 | 10275.78 ± 1530.22 |
| | AZT-resistant HIV-1 018c | AKJ-1 | 5.55 ± 0.136 | 0.97 ± 0.13 | 5.75 ± 0.67 |
| | | AKJ-2 | 5.83 ± 0.38 | >1.25 ± 0 | — |
| | | AZT | 87.97 ± 15.54 | 0.05 ± 0.01 | 1895.40 ± 479.53 |
| H9 Cell Chronically Infected with HIV-1 IIIB | HIV-1 IIIB | AKJ-1 | 1.915 ± 0.09 | >0.25 ± 0 | — |
| | | AKJ-2 | 1.77 ± 0.13 | >0.25 ± 0 | — |
| | | AZT | >85.39 ± 20.66 | 1.08 ± 0.24 | 83.65 ± 37.96 |

It was observed from the aforesaid results that using the anti-HIV-1 medicament as the positive control, the shikonin compounds according to this invention were effective in the passage human T-lymphocytes MT-4 culture infected with HIV-1 IIIB and in H9 cell culture chronically infected with HIV-1 IIIB. In the 018a/018c-infected PBMC culture, AZT was more active to the sensitive strain than to the resistant strain.

In addition, shikonin compounds had certain inhibition effect on the reproduction of HIV-1 in passage human T-lymphocytes MT-4 culture infected with HIV-1 IIIB and PBMC culture infected with HIV-1 018a. As shown by two lots of tests using the HIV-1 IIIB chronically-infected H9 cells, AKJ-1 and AKJ-2 had no inhibition effect on the HIV-1 IIIB chronically-infected H9 cells, so the median effective concentration ($EC_{50}$) could not be calculated.

Efficacy of Shikonin Compounds on SARS Viruses

1. Selection of Subjects:

Patients that had been diagnosed as SARS sufferers with severe symptoms and had the similar degree of illness were selected as subjects, and these patients were capable of swallowing. 20 patients aging from 19 to 59 years old were preferentially selected and divided into two groups with ten in the test group and ten in the control group.

2. Treatment Protocol:

For the test group: the original prescription by the hospital+ Kedu Capsule which contained 300 mg/capsule, including shikonin, one of β,β-dimethyl-acry-shikonin and acetylshiuonin or their mixture (50 mg/ capsule) (two capsules once, thrice a day; postprandial oral administration). Among them, five took the Kedu Capsule for ten days after the disease attack. Period of Treatment: 10 days For the control group: the original prescription by the hospital.

3. Treatment Results

As observed from Table 7 below, the average course of disease of the test group was 33 days (including the observation period), while for the control group, it was 39 days. Therefore, it can be appreciated that the average course of disease for the test group was 6 days, or 15%, shorter than that of the control group. The average course of disease for patients that had taken Kedu Capsule within ten days after the disease attack was 11 days, or 28%, shorter than that of the control group. Kedu Capsule would be more effective if it was taken earlier. As demonstrated by the data, the duration of the course of disease had a direct correlation with the time taking the medicament. The earlier the medicament was taken, the shorter the course of disease was. The course of disease for patients having the administration period less than 10 days was shorter than the average of that of the control group. While the course of disease for patients having the administration period equal to or more than 10 days was equal to that of the control group.

TABLE 7

Relation between Kedu Capsule-taking Time and Course of Disease of SARS Patients

| Number | 1 | 2 | 3 | 4 | 5 | 6 | 7 | 8 | 9 | 10 | Average | r |
|---|---|---|---|---|---|---|---|---|---|---|---|---|
| Age/gender | 26 f | 19 m | 21 f | 59 f | 40 m | 44 f | 48 m | 35 f | 26 m | 26 m | | |
| Administration Period ($x_i$) | 2 | 3 | 7 | 9 | 9 | 10 | 11 | 14 | 17 | 18 | 10. | 0.87 |
| Reproduction Period ($t_i$) | 2 | 3 | 7 | 9 | 9 | 10 | 11 | 11 | 11 | 11 | 8. | 0.96 |
| Course of Disease ($y_i$) | 21 | 22 | 26 | 28 | 35 | 38 | 41 | 37 | 42 | 39 | 33 | |

TABLE 7-continued

Relation between Kedu Capsule-taking Time and Course of Disease of SARS Patients

| Number | 1 | 2 | 3 | 4 | 5 | 6 | 7 | 8 | 9 | 10 | Average | r |
|---|---|---|---|---|---|---|---|---|---|---|---|---|
| $Lny_i$ | 3.04 | 3.09 | 3.26 | 3.33 | 3.56 | 3.64 | 3.71 | 3.61 | 3.74 | 3.66 | 3.46 | 0.98 |
| Control group (y) | Female, 8; male, 2; 18-30 years old, 5; 31-50 years old, 5 | | | | | | | | | | 39 | |

Note:
1) The administration period (x) refers to the interval between the disease attack time and the Kedu Capsule-taking time.
2) The reproduction period (t) refers to the interval between the disease attack time and the reproduction cessation time of the virus [supposed t = x(x ≦ 11), t = 11 (x ≧ 11)];
3) Course of disease (y) refers to the interval from the disease attack time to the leave-hospital time (observation period after the healing is included).
4) Lny is the logarithm value of y.
5) Contrast (y) is the average course of disease of ten patients in the control group.
6) r is the correlation coefficient between the Kedu Capsule-taking time and the course of disease.
7) f stands for female.
8) m stands for male.

The aforesaid tests have shown that administering Kedu Capsule at the early stage of SARS has significant efficacy. Preferably, the medicament should be taken within one week after the disease attack. Judging from the iconography result, it was clear that the status of SARS infected lungs in the control group had worsened in five cases during the hospitalization period. Although in the test group, one case also had such a condition, however, the patient's condition was less severe. This indicated that even if the patients started taking the instant medicament beyond the early state of the disease, it was better than not taking the medicament at all. Based on this observation, inhibiting or killing the virus not only releases symptoms from the patients, but also enhances the recovery function of the human bodies. Moreover, the Kedu Capsule functions in inhibiting and killing fungi, therefore, double infection from fungi can also be avoided, which can be appreciated from the comparison between the mean values of the test group and the control group.

What is claimed is:

1. A method of treating a virus infection comprising administering to a subject infected with SARS virus an effective amount of a composition comprising one or more shikonin compounds represented by formula (1), wherein R is H, OH, $(CH_3)_2C$=$CHC(O)O$—, $CH_3C(O)O$—, $(CH_3)_2C$=$C(CH_3)CH_2C(O)O$—, $(CH_3)_2$ $COHCH_2C(O)$ $O$—, or $(CH_3)_2C[OC(O)CH_3]CH_2C(O)O$—, and wherein said effective amount of said composition is from 100 μg to 10 g of said one or more shikonin compounds daily.

2. The method of claim 1, wherein said R is OH, $(CH_3)_2$ $C$=$CHC(O)O$—, or $CH_3C(O)O$—.

3. The method of claim 1, wherein said effective amount of said composition is from 1 mg to 8 g of said one or more shikonin compounds daily.

* * * * *